United States Patent [19]

Lockhoff et al.

[11] Patent Number: 4,710,491

[45] Date of Patent: Dec. 1, 1987

[54] N-GLYCOSYLATED CARBOXYLIC ACID DERIVATIVES AS AGENTS FOR COMBATING RHEUMATIC DISEASES

[75] Inventors: Oswald Lockhoff, Cologne; Peter Stadler, Haan, both of Fed. Rep. of Germany; Hans-Georg Opitz, Berkeley, Calif.; Harald Horstmann; Bodo Junge, both of Wuppertal, Fed. Rep. of Germany; Bernhard Pelster, St. Augustin, Fed. Rep. of Germany

[73] Assignee: Troponwerke GmbJ & Co., KG, Cologne, Fed. Rep. of Germany

[21] Appl. No.: 681,965

[22] Filed: Dec. 14, 1984

[30] Foreign Application Priority Data

Dec. 30, 1983 [DE] Fed. Rep. of Germany ....... 3347522

[51] Int. Cl.$^4$ ............................................. A61K 31/70
[52] U.S. Cl. ...................................... 514/42; 536/22
[58] Field of Search .......................................... 514/42

[56] References Cited

FOREIGN PATENT DOCUMENTS 0091645 10/1983 European Pat. Off. .............. 514/42
0147777  7/1985 European Pat. Off. .............. 514/42

OTHER PUBLICATIONS

Paulus et al., "Arthritis Rheum.", vol. 20, 1977, pp. 1249–1262.
Bunch et al., "Mayo Clin. Proc.", vol. 55, 1980, pp. 161–179.
Kotzin et al., "New Engl. of Med.", vol. 305, 1981, pp. 969–976.

Primary Examiner—J. R. Brown
Assistant Examiner—L. Eric Crane
Attorney, Agent, or Firm—Sprung Horn Kramer & Woods

[57] ABSTRACT

A method of combating rheumatic diseases which comprises administering to a patient afflicted therewith an amount effective to combat such disease of a compound of the formula

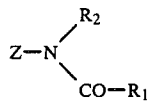

in which
Z is a glycosyl radical bonded via the anomeric carbon atom,
$R_1$ is hydrogen or an optionally substituted hydrocarbon radical with up to 30 C atoms, which hydrocarbon radical is optionally interrupted by O, N or S, and
$R_2$ is hydrogen or an alkyl or aralkyl radical with up to 30 C atoms, which is optionally interrupted by O, N or S or substituted by an oxygen-containing group or halogen,
with the proviso that $COR_1$ is not an acyl group with 1–5 C atoms if $R_2$ is alkyl with 10–20 C atoms.

8 Claims, No Drawings

N-GLYCOSYLATED CARBOXYLIC ACID DERIVATIVES AS AGENTS FOR COMBATING RHEUMATIC DISEASES

The present invention relates to the use of compounds of the general formula I

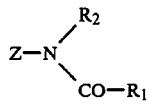

as agents for combating rheumatic diseases. In the general formula I, $R_1$ denotes hydrogen or an optionally substituted straight-chain or branched, saturated or mono- or poly-unsaturated alkyl radical with 1 to 30 carbon atoms, it also being possible for this radical $R_1$ to be interrupted by up to 5, preferably 1 or 2, O, S and/or N atoms If the chain is interrupted by N, this nitrogen carries either H or a $C_1$-$C_{20}$-alkyl radical, preferably a $C_1$-$C_5$-alkyl radical, or a —CO—alkyl radical, this alkyl group containing 1-20, preferably 1-5, C atoms.

$R_1$ is preferably an alkyl or alkenyl radical with 1 to 21 carbon atoms, preferably with 9 to 21 C atoms. Examples which may be mentioned here of saturated radicals are methyl, ethyl, propyl, i-propyl, butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, ethylpentyl, methyldecyl, i-propyldecyl and methyltridecosyl.

Examples of unsaturated radicals are vinyl, prop-1-enyl, prop-2-enyl, i-butenyl, but-1-enyl, but-2enyl, pent-1-enyl, pent-2-enyl, pent-3-enyl, pent-4-enyl, hex-1-enyl, hex-2-enyl, hex-3-enyl, hex-4-enyl, hex-5-enyl, dec-1-enyl, dec-5-enyl, dec-9-enyl, heptadec-8-enyl, buta-1,3-dienyl, penta-1,3-dienyl, penta-1,4-dienyl, penta-2,4-dienyl, heptadecane-8,11-dienyl and heptadecane-8,11,14-trienyl. The longer-chain, unsaturated radicals, especially the mono- or di-unsaturated alkenyls with 7–21 C atoms, are generally preferred.

The unsaturated hydrocarbon radicals can be in the form of pure cis or trans isomers or also in the form of isomer mixtures.

Examples of cases where the hydrocarbon radicals $R_1$ in formula I are interrupted by O, S and N or corresponding atom groupings or are substituted by groups containing these atoms or by halogen atoms are the methoxyethyl, 2-(2-methoxyethoxy)-ethyl, 2-[2-(2-methoxyethoxy)ethoxy]-ethyl, hydroxyheptadecenyl, oxobutyl, aminodecyl, N-methylaminodecyl, fluoromethyl, β-hydroxytridecyl and mercaptoethyl radicals.

The hydrocarbon radicals $R_1$ in formula I can also contain phenyl radicals, it being possible for these phenyl radicals optionally also to be substituted by one to three substituents from the series comprising nitro and lower alkyl or by 1–5 halogen atoms.

$R_2$ in formula I represents hydrogen or a straight-chain or branched, saturated or mono- or poly-unsaturated alkyl, cycloalkyl or alkylcycloalkyl or an aralkyl radical with up to 30 carbon atoms, it also being possible for individual methylene or methine groups in the radical $R_2$ to be replaced by up to 5 oxygen or sulphur atoms or N, NH or N-lower alkyl groupings. Individual hydrogen atoms in the alkyl, cycloalkyl or aralkyl radicals can also be replaced by up to 5 oxygen-containing groups or halogen atoms.

Examples in which $R_2$ in formula I represents a straight-chain or branched, optionally mono- or poly-unsaturated alkyl radicals are those mentioned for $R_1$.

Radicals which may be mentioned in particular are methyl, propyl, hexyl, decyl, undecyl, dodecyl, tridecyl, tetradecyl, pentadecyl, hexadecyl, heptadecyl, octadecyl, nonadecyl, docosyl, myricyl, ethylhexyl, isobutyl, propenyl, octenyl, hexadienyl, docosenyl, dimethylhexenyl and 2-(cyclohexyl)-ethyl. The unsaturated hydrocarbons radicals can be in the form of pure cis or trans isommers or in the form of an isomer mixture. Examples of hydrocarbon radicals $R_2$ which are substituted by groups containing oxygen atoms are hydroxypropyl and hydroxydimethyloctyl, examples of hydrocarbon radicals which are interrupted by oxygen atoms are alkoxyalkyl radicals or (alkoxy-alkoxy)-alkyl radicals, such as methoxybutyl, butoxypropyl and ethoxyethoxyethyl, an example of a radical interrupted by N and O is 2-(N-morpholino)-ethyl and an example which may be mentioned of a halogen-substituted hydrocarbon radical is trifluoromethylethyl.

Aralkyl $R_2$ in formula I is, for example, aryl-lower alkyl, such as benzyl, phenethyl or phenylhexyl, it being possible for the phenyl nucleus optionally to be mono- or poly-substituted, preferably mono- or di-substituted, for example by lower alkyl, trifluoromethyl, halogen, hydroxyl or lower alkoxy.

Lower alkyl or alkoxy in the context of the present invention are understood as meaning those radicals which contain 1–5, preferably 1–3, C atoms.

Z in formula I denotes a glycosyl radical which, in the compounds according to the invention, is always bonded to the amide nitrogen via the anomeric carbon atom, glycosyl radicals according to the invention being understood particularly as meaning mono-, di- or oligosaccharide radicals, in particular monosaccharides and disaccharides, in which one or more hydroxyl groups can be replaced by amino groups, acylamido groups, azido groups, hydrogen, nitro, thiol groups or lower alkoxy or halogen, and it being possible for the glycosyl radicals also to be in the form of the corresponding uloses, ulose derivatives, uronic acids or uronic acid derivatives.

According to the invention, the glycosyl radicals Z in formula I are preferably in the pyranosyl or furanosyl form, the monosaccharide, disaccharide or oligosaccharide radicals in question preferably being built up from tetroses, pentoses, hexoses and heptoses.

Examples according to the invention of monosaccharide radicals are glucopyranosyl, galactopyranosyl, mannopyranosyl, glucofuranosyl, ribofuranosyl, arabinopyranosyl, lyxopyranosyl and D-glycero-D-gluco-heptopyranosyl radicals. Examples of di- and oligosaccharide radicals which may be mentioned are maltosyl-, maltotriosyl-, maltotetraosyl-, lactosyl-, cellobiosyl-, melibiosyl- or 6-0-(α- or β-ribofuranosyl)-glucopyranosyl radicals, that is to say carbohydrate systems which are built up from sugars of different C numbers and in which the sugars can be in the pyranose and/or furanose form. The glycosidic bonds between the individual sugar units can be in the α- and/or β-form and the glycosidic linkage of the individual sugar units can start from an anomeric carbon atom and be either via the primary OH group or via one of the secondary hydroxyl groups of the saccharide portion functioning as the aglycone.

Examples which may be mentioned of mono-, di- or oligosaccharide radicals in which one or more OH groups are replaced by amino groups, acylamido groups, azido groups, hydrogen, nitro, thiol groups, lower alkoxy or halogen are 2-acetylamido-2-deoxyglucopyranosyl, 2-amino-2-deoxy-glucopyranosyl, 4-azido-4-deoxy-glucopyranosyl, 4-stearoylamido-4-deoxy-D-glucopyranosyl, 4-dodecoylamido-4-deoxy-D-glucopyranosyl, 6-hexadecanoylamido-6-deoxy-D-galactopyranosyl, 2,6-diamino-2,6-dideoxyglucopyranosyl, 6,6'-diamino-6,6'-dideoxymaltosyl, 6-amino-6,6'-dideoxylactosyl, 6-deoxymannopyranosyl, 2-deoxyribofuranosyl, fucosyl, 5-fluoro-5-deoxyribofuranosyl, 6-0-methylglucopyranosyl, 6-deoxy-6-thio-glucopyranosyl and 3-deoxy-3-nitrogalactopyranosyl.

If the glycosyl radicals are in the form of uronic acids or uronic acid derivatives, these are glycuronic acids with a free carboxyl group or with a carboxyl group esterified by alkyl, or glycuronamide derivatives with an unsubstituted or substituted nitrogen atom. EXAMPLEs of corresponding sugars are galacturonic acid, methyl glucuronate, glucuronamide and N-dodecyl-glucuronamide.

The compounds of the formula I contain several chiral C atoms and are in the form of optical pure diasteromers or in the form of diasteromer mixtures. The compounds of the formula I according to the invention are thus carboxylic acid amides or N-alkylated or N-aralkylated carboxylic acid amides, each of which carries a simple or modified mono-, di- or oligo-saccharide radical N-glycosidically —that is to say bonded via the anomeric carbon atom —on the amide nitrogen.

The compounds documented by the embodiment examples, in particular the compounds of EXAMPLEs 12, 13, 14, 15, 16, 18, 20, 24, 26, 34, 35, 36, 38, 40, 41, 43, 44, 46, 47, 49, 50, 51, 54, 55, 56, 57, 58 and 60, are very particularly preferably used as antirheumatics.

The compounds of the formula I can be prepared by the following processes: the sugar represented by Z in formula I is first reacted, either in the free form, that is to say in the unprotected form, or in the form of protected, optionally activated derivatives, with an amino compound $R_2$—$NH_2$, either in the free form or in the form of a suitable acid addition salt, with the meaning for $R_2$ described above, and the glycosylamine thereby obtained is then acylated with a carboxylic acid derivative which is activated —as is customary in acylation reactions —and optionally protected on functional groups, and any protective groups present in the reaction product thus obtained are split off to give, in this manner, the compounds of the formula I, which can be purified, if necessary, by chromatography, recrystallization, extraction or the like.

The following equation is intended to illustrate one of the preferred embodiments of the preparation of compounds of the formula I by way of example:

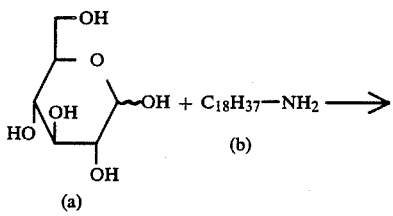

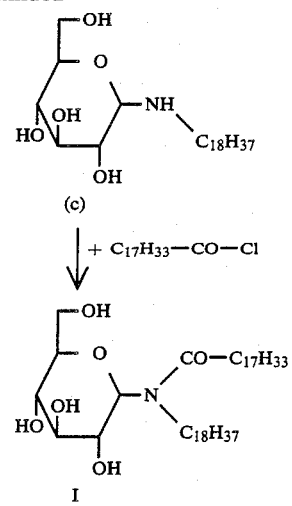

In the first process step, glucose (a) is reacted with octadecylamine (b) to give N-octadecyl-β-D-glucopyranosylamine (c), which is acylated with oleoyl chloride in the second process step to give N-octadecyl-N-oleoyl-β-D-glucopyranosylamide (I). The invention also relates to the use of the compounds of the formula I or of the salts of the compounds of the formula I as agents in combating rheumatic diseases. These salts are above all usually pharmaceutically usable, non-toxic salts, for example the alkali metal, ammonium or alkaline earth metal salts.

The compounds of the formula I have valuable properties which render them useful for combating rheumatic diseases. It has been possible to demonstrate this with the aid of the experimental design described below.

In an experiment lasting four weeks, the anti-arthritic action of compounds of the formula I was investigated on the model of Freund's adjuvant arthritis in rats. The active compound was administered intraperitoneally every day. The action criteria were: body weights, swelling of the right and left hind paw, ankle joint cross-infection and haematological parameters.

In the second half of the experiment, the active compounds clearly reduced the decrease in body weight which usually occurs after administration of Freund's adjuvant, and inhibited the swelling of the right and left hind paw in a dose-dependent manner. Towards the end of the experiment, the swelling in the left paw of rats which had received undiluted product disappeared completely. The undiluted formulation reduced the ankle joint cross-infection in the 2nd–4th week.

The use of the compounds N-glucosyl-N-octadecyl-dodecanoic acid amide and/or N-tetradecyl-N(2-amino-2-deoxy-D-glucopyranosyl)-stearic acid amide as agents in combating rheumatic diseases is preferred according to the invention.

The pharmaceutical products of the present invention are preferably tablets or gelatin capsules which contain the active compounds together with diluents, for example lactose, dextrose, sucrose, mannitol, sorbitol or cellulose, and/or lubricants, for example silica, talc, stearic acid or salts thereof, such as magnesium stearate or calcium stearate, and/or polyethylene glycol. Tablets also contain binders, for example magnesium aluminium silicate, starches, such as wheat starch, corn starch, rice starch or arrowroot starch, gelatin, traganth methylcellulose or sodium carboxymethylcellulose, and/or polyvinylpyrrolidone, and, if desired, disintegrating agents, for example starches, agar, alginic acid or a salt thereof, such as sodium alginate, and/or effervescent mixtures, or adsorbents, colorants, flavoring agents and sweeteners. Injectable products are preferably isotonic aqueous solutions or suspensions. Suppositories, ointments or creams are, above all, fat emulsions or suspensions. The substances can furthermore be incorporated into liposomes, which have proved themselves in animal experiments. The pharmaceutical product can be sterilized and/or contain auxiliaries, for example preservatives, stabilizers, wetting agents, emulsifying agents, solubilizing agents, salts for regulating the osmotic pressure and/or buffers. The present pharmaceutical products, which, if desired, can contain other pharmacologically useful substances, are prepared in a manner which is known per se, for example by means of conventional mixing, granulating or tablet-coating processes, and contain about 0.1% to about 75%, in particular about 1% to 50%, of the active substances mentioned.

The orally administered products of the present invention can also be provided with a coating which is resistant to gastric juice.

The compounds according to the invention can be used as agents for combating rheumatic diseases.

The following examples illustrate the invention described above, but are not intended to restrict the scope of this invention in any manner.

The invention also generally relates to the salts of the compounds I with any other salt-forming groups, for example free carboxyl groups, above all pharmaceutically useful, non-toxic salts, for example metal or ammonium salts, in their use as antirheumatics or corresponding formulations or agents.

EXAMPLES

The thin layer chromatography (TLC) was carried out on TLC silica gel pre-coated plates (E. Merck, Darmstadt) and the preparative chromatography was carried out with silica gel 60 (Merck, Darmstadt).

Eluting agent systems: System G $CH_2Cl_2/CH_3OH/15\%$ strength ammonium hydroxide in a ratio of 1:1:1, the lower phase from this; system E $CH_2Cl_2/CH_3OH/20\%$ strength ammonium hydroxide in a ratio of 8:4:1; in each case parts by volume.

EXAMPLE 1

N-D-Glucopyranosyl-oleic acid amide 3 g of 2,3,4,6-tetra-0-acetyl-$\beta$,D-glucopyranosylamine were dissolved in 25 ml of tetrahydrofuran and, after addition of 3.45 g of sodium carbonate, 2.24 g of oleoyl chloride, dissolved in 5 ml of tetrahydrofuran (THF), were added dropwise at 0° C., with vigorous stirring and cooling. When the reaction was complete (checked by thin layer chromatography=TLC in the system toluene: acetone=4:1), the precipitate was filtered off, the filtrate was evaporated in vacuo and the residue was dried. For 0-deacetylation, the crude product thus obtained was dissolved in 200 ml of a solution of methanol/triethylamine/water=4:3:1 (parts by volume) and the solution was left at room temperature for 15 hours. It was then evaporated in vacuo and the residue was chromatographed on silica gel. The title product obtained in this manner had an Rf value of 0.46.

EXAMPLE 2

N-Benzyl-$\beta$-D-glucopyranosylamine 50 g of D-glucose were dissolved in 1,000 ml of hot ethanol and, after addition of 89 g of benzylamine, the mixture was left at room temperature for 48 hours. It was then cooled with ice and the product was precipitated with petroleum ether. The product was filtered off with suction, washed with ether and dried in vacuo. $^1$H-NMR in $CD_3OD$: $\delta = 7.33$, broad singlet, phenyl-H.

EXAMPLE 3

N-Benzyl-N-glucopyranosyl-acetamide 1 g of the compound from EXAMPLE 2 was acylated in 10 ml of absolute pyridine and 6 ml of acetic anhydride at 0° C. for 1 hour and then at room temperature. The product was worked up in the customary manner to give 1 g of the N-acetyl-tetra-0-acetyl derivative. $^1$H-NMR in $CD Cl_3$: $\delta = 1.9-2.1$ m $5 \times CH_3$—CO—.

For 0-deacetylation, 500 ml of the pentaacetate were deacetylated with 10% of sodium methanolate in absolute methanol and the product was worked up in a customary manner. The product was obtained as an amorphous solid. $^1$H-NMR in $CD_3OD$: $\delta = 7.1-7.4$ phenyl-H.

EXAMPLE 4

N-Dodecyl-$\beta$D-glucopyranosylamine 18 g of glucose were stirred in 50 ml of ethanol at 70° C., 18.5 g of dodecylamine were then added, the mixture was heated again until a clear solution was obtained, the solution was allowed to cool to room temperature and, after 20 hours, the crystals which had precipitated were filtered off with suction. The product was washed with ethanol and ether and dried in vacuo. Yield=24 g.

Elemental analysis: ($C_{18}H_{37}NO_5 = 347$): calculated C=62.2%, H=10.6%, N=4.0%; found C=62.2%, H=10.6%, N=4.2%.

EXAMPLE 5

N-Dodecyl-N-$\beta$-D-glucopyranosyl-acetamide

The preparation was carried out analogously to Example 3.

Elemental analysis: calculated: C=61.7%, H=10.0%, N=3.6%; found: C=60.8%, H=9.9%, N=3.8%.

EXAMPLE 6

N-Glucopyranosyl-N-propyl-oleic acid amide 11 g of N-propyl-D-glucopyranosylamine were stirred with 21 g of sodium carbonate in 90 ml of tetrahydrofuran (THF), and 1 equivalent of oleoyl chloride in 20 ml of THF was then slowly added dropwise, with cooling. When the N-acylation was complete (checked by TLC in the eluting agent system $CH_2Cl_2/CH_3OH = 13:1$), the precipitate was filtered off with suction and rinsed with THF, the filtrates were evaporated in vacuo and the resulting syrup was chromatographed on silica gel for subsequent purification. The column was developed with $CH_2Cl_2/CH_3OH = 15:1$.

The fractions which contained pure title compound were combined. The solvent was removed in vacuo. Yield: 3.3 g.

Rf value: 0.34 in $CH_2Cl_2/CH_3OH=15.1$.
$[\alpha]_D^{20}=+7.5°$ (c=1.0, $CH_2Cl_2$).

EXAMPLE 7

N-Glucopyranosyl-N-hexyl-oleic acid amide

The preparation was carried out, starting from N-hexyl-D-glucopyranosylamine, as described in Example 6. Column chromatography with $CH_2Cl_2/CH_3OH=13:1$.
Yield: 9.2 g of pure product.
Rf value=0.38 in $CH_2Cl_2/CH_3OH=13:1$.
$[\alpha]_D^{20}=+5.8°$ C. (c=0.94 in $CH_2Cl_2$).

EXAMPLE 8

N-Glucopyranosyl-N-(n-3,3,3-trifluoropropyl)-oleic acid amide 3.6 g of glucose, 0.8 ml of 0.5N hydrochloric acid and 4.6 g of n-3,3,3-trifluoropropylamine were heated at 75° C. for 25 minutes, with stirring. After cooling, the N-glucoside crystallized out, and was washed with ether and dried in vacuo.
Yield: 4.1 g.
The N-acylation with oleoyl chloride was carried out analogously to Example 6. Column chromatography with $CH_2Cl_2/CH_3OH=15:1$.
Yield: 2.7 g.
$[\alpha]_D^{20}=+7.6°$ (c=1.0 in $CH_2Cl_2$).

EXAMPLE 9

N-(2-Ethyl-hexyl)-N-glucopyranosyl-oleic acid amide

The reaction of glucose with 2-ethyl-hexylamine was carried out analogously to Example 8. The N-acylation with oleoyl chloride was carried out analogously to Example 6. Column chromatography with $CH_2Cl_2/CH_3OH=15:1$.
Rf value of the title compound: 0.44 in $CH_2Cl_2/CH_3OH=15:1$.

EXAMPLE 10

N-(3-Butoxy-propyl)-N-glucopyranosyloleic acid amide

Preparation of the N-glycoside and N-acylation as described for Example 8 and Example 6.
Rf value: 0.29, eluting agent system $CH_2Cl_2/CH_3OH=10/1$.

EXAMPLE 11

N-Dodecyl-N-glucopyranosyl-stearic acid amide 100 g of N-dodecyl-β-D-glucopyranosylamine from EXAMPLE 4 were dissolved in 765 ml of THF, and 80 g of stearoyl chloride were added dropwise in the presence of 32 g of triethylamine, with cooling.
For working up, the mixture was filtered and the solvent was removed in vacuo.
N-Dodecyl-N-glucopyranosyl-oleic acid amide was likewise prepared.

EXAMPLE 12

N-Decyl-N-glucopyranosyl-oleic acid amide 18 g of D-glucose and 50 ml of ethanol were stirred with 15.7 g of decylamine at 70° C. until a clear solution was obtained. The solution was then allowed to cool to room temperature and, after 4 hours, the crystals were filtered off with suction and rinsed with ethanol and ether. Yield: 20 g These crystals were stirred in 166 ml of THF with 22.6 g of sodium carbonate. 19 g of oleoyl chloride in 20 ml of THF were then slowly added dropwise at 25° C. After a further hour, the precipitate was filtered off with suction, the filtrate was evaporated to a syrup in vacuo and the crude product was purified by column chromatography on silica gel using the eluting agent $CH_2Cl_2/CH_3OH=13/1$.
Rf value of the title compound=0.53 in $CH_2Cl_2/CH_3OH=13:2$.

EXAMPLE 13

N-Glucopyranosyl-N-tetradecyl-oleic acid amide

The preparation is analogous to Example 12.
Column chromatography with the eluting agent $CH_2Cl_2/CH_3OH=13/1$.
$[\alpha]_D^{20}=+9.6$ (c=1.0, dimethylformamide)
Elemental analysis: calculated C=70.3%, H=11.3%, N=2.16%; found C=69.4%, H=11.6%, N=2.1%.

EXAMPLE 14

N-glucopyranosyl-N-hexadecyl-oleic acid amide

The preparation and purification are analogous to Example 12.
Rf value 0.25, eluting agent $CH_2Cl_2/CH_3OH=13:1$.

EXAMPLE 15

N-Glucopyranosyl-N-octadecyl-oleic acid amide 90 g of D-glucose and 135 g of octadecylamine were heated at 50° C. in 1,000 ml of 2-propanol and 500 ml of water, with stirring, until a clear solution was formed. The solution was then left at room temperature overnight. The product was now filtered off with suction, washed with alcohol and ether, dried and, finally, recrystallized from ethanol/THF. 10 g of this N-octadecyl-β-D-glucopyranosylamine were suspended in 80 ml of THF and, after addition of 10 g of sodium carbonate, 7 g of oleoyl chloride in 10 ml of THF were added dropwise. After quantitative reaction (TLC in $CH_2Cl_2/CH_3OH=13/1$), the product was worked up as described in Example 12. Column purification with the eluting agent $CH_2Cl_2/CH_3OH=13/1$.
RF value=0.35, eluting agent system $CH_2Cl_2/CH_3OH=9/1$.

EXAMPLE 16

N-Glucopyranosyl-N-octadecyl-stearic acid amide

The preparation is analogous to Example 6, from N-octadecyl-glucopyranosytamine and stearoyl chloride.
Elemental analysis: calculated: C=72.5%, H=11.7%, N=2.0%; found: C=71.7%, H=12.2%, N=2.0%.

EXAMPLE 17

N-Glucosyl-N-octadecyl-dodecanoic acid amide

The preparation is analogous to Example 16, from N-octadecyl-β-D-glucopyranosylamine and dodecanoic acid chloride.
$[\alpha]_D^{20}=+8°$ (C=1.0, dioxane).

EXAMPLE 18

N-Glucosyl-N-octadecyl-tetradecanoic acid amide

The preparation is analogous to Example 16 from from N-octadecyl-β-D-glucopyranosylamine and tetradecanoic acid chloride.

$[\alpha]_D^{20} = +9.5°$ (c=1.0, DMF).

Elemental analysis: calculated: C=71.8%, H=11.7%, N=2.1%; found: C=71.3%, H=11.9%, N=1.9%.

EXAMPLE 20

N-(2-Acetamido-2-deoxy-D-glucopyranosyl)-N-octadecyl-oleic acid amide 15 g of N-acetyl-D-glucosamine and 18.8 g of octadecylamine were heated at 80° C. in 50 ml of ethanol for 3 hours, with stirring. The undissolved material was then filtered off hot, the filtrate was cooled and the product which had precipitated was filtered off with suction and washed with ethanol and ether. 2.2 g of the 2-acetamido-2-deoxy-N-octadecyl-glucopyranosylamine thus obtained were stirred in 17 ml of THF with 2 g of sodium carbonate. 1.45 g of oleoyl chloride in 5 ml of THF were then added dropwise.

The product was worked up as described in Example 6. Column chromatography with the eluting agent $CH_2Cl_2/CH_3OH = 20:1$.

$[\alpha]_D^{20} = +15.5°$ (c=1.0, THF).

Elemental analysis: calculated: C=71.7%, H=11.5%, N=3.8 %; found: C=71.9 %, H=11.6 % N=3.6 %.

EXAMPLE 21

N-Octadecyl-L-rhamnopyranosylamine 9 g of L-rhamnose and 13.5 g of stearylamine were stirred in 100 ml of 2-propanol and 50 ml of water at 50° C. until a clear solution had formed. After 50 hours at room temperature, the crystals were filtered off with suction, washed with ethanol and ether and dried in vacuo.

Yield: 17.4 g.

EXAMPLE 22

N-Octadecyl-N-rhamnopyranosyl-oleic acid amide 7 g of the compound from Example 21 were acylated with oleoyl chloride as described in Example 6. Column separation in $CH_2Cl_2/CH_3OH = 13/1$.

Elemental analysis: calculated: C=74.4%, H=11.9%, N=2.04%; found: C=74.3%, H=12.0%, N=2.1%..

EXAMPLE 23

N-Octadecyl-L-fucopyranosylamine 3.26 g of L-fucose and 5.38 g of stearylamine were heated at 70° C. in 20 ml of ethanol, with stirring, until a clear solution had formed. The solution was allowed to cool and, when crystallization had ended, the solid was filtered off with suction and washed with ethanol and ether.

Yield after drying in vacuo: 4.4 g.

EXAMPLE 24

N-Fucopyranosyl-N-octadecyl-oleic acid amide 2.9 g of the compound from Example 23 were acylated with oleoyl chloride as described in Example 6.

Column chromatography with the eluting agent $CH_2Cl_2/CH_3OH = 15/1$.

Yield of pure product: 1.9 g.

RF value=0.44, eluting agent system as for the column chromatography.

EXAMPLE 25

N-β-D-Arabinopyranosyl-N-octadecyl-oleic acid amide 7 g of N-octadecyl-β,D-arabinopyranosylamine were acylated with oleoyl chloride as described in Example 6. Column chromatography with the eluting agent $CH_2Cl_2/CH_3OH = 20/1$.

Yield of pure product: 2.3 g.

RF value=0.57, eluting agent $CH_2Cl_2/CH_3OH = 15:1$.

$[\alpha]_D^{20} = +20°$ (c=1.03, $CH_2CC_2$).

EXAMPLE 26

N-β-D-Maltosyl-N-octadecyl-oleic acid amide 3.04 g of N-octadecyl-β-D-maltosylamine were acylated with oleoyl chloride as described in Example 6. Column chromatography in $CH_2Cl_2/CH_3OH = 10/1$.

RF value: 0.24, eluting agent $CH_2Cl_2/CH_3OH = 8.1$.

$[\alpha]_D^{20} = +22°$ C. (c=0.5, $CH_3OH$).

EXAMPLE 27

N-(4-Azido-4-deoxy-D-glucopyranosyl)-N-octadecyl-dodecanoic acid amide 3.09 g of 4-azido-4-deoxy-D-glucose were dissolved in 30 ml of isopropanol and 15 ml of water and, after addition of 4.05 g of octadecylamine, the mixture was warmed to 50° C.

The solution formed was left to stand at room temperature overnight. The resulting solid was filtered off, rinsed with a little ethanol and ether and dried.

2.3 g of this product were dissolved in 10 ml of THF, and 3 g of sodium carbonate and 1.2 g of dodecanoic acid chloride, dissolved in 15 ml of THF, were added. After quantitative reaction, the product was worked up as described in Example 12.

Rf value: 0.27 in $CH_2Cl_2/CH_3OH = 4:1$ (V/V).

EXAMPLE 28

N-(4-Acetamido-4-deoxy-D-glucopyranosyl)-N-octadecyl-dodecanoic acid amide.

3 g of the compound from Example 27 were hydrogenated in 30 ml of dioxane/methanol=2:1 and 3 ml of acetic anhydride in the presence of 1.0 g of palladium-on-charcoal (5%) under normal pressure. When the reaction had ended (eluting agent system $CH_2Cl_2/CH_3OH = 3:1$) the catalyst was filtered off with suction and the filtrate was concentrated in vacuo.

Rf value: 0.18 ($CH_2Cl_2/MeOH$, 10:1 V/V).

EXAMPLE 29

N-(6-Deoxy-6-fluoro-D-glucopyranosyl)-N-octadecyl-oleic acid amide 18.2 g of 6-deoxy-6-fluoro-D-glucose, 13.5 g of octadecylamine and 7 g of oleoyl chloride were reacted as described in Example 15 and the product was worked up.

Rf value: 0.30 in $CH_2Cl_2/CH_3OH = 9/1$.

EXAMPLE 30

N-(Methyl-D-glucopyranosyluronato)-N-octadecyl-oleic acid amide 15 g of D-glucuronolactone were dissolved in 150 ml of absolute methanol and the solution was left to stand with 3 ml of 1 N sodium methanolate solution at room temperature for half an hour. The mixture was then neutralized with an acidic ion exchanger and evaporated. The resulting methyl glucuronate was reacted and worked up to give the title compound as described in Example 15.

Rf value: 0.32 ($CH_2Cl_2/CH_3OH=9:1$, V/V).

EXAMPLE 31

N-(Glucuronopyranosyl)-N-octadecyl-oleic acid amide 2 g of the compound described in Example 30 were dissolved in 10 ml of dioxane and, after addition of 5 ml of 1 N sodium hydroxide solution, the mixture was heated under reflux for 2 hours. After cooling, it was neutralized with dilute hydrochloric acid and concentrated in vacuo and the residue was stirred with 20 ml of methanol/dioxane=1:1. The mixture was then filtered and the filtrate was concentrated to a syrup.

Rf value: 0.13 ($CH_2Cl_2/CH_3OH=7:1$, V/V).

EXAMPLE 32

N-(4-Amino-4-deoxy-D-glucopyranosyl)-N-octadecyl-lauric acid amide 3 g of the compound from Example 27 were hydrogenated in 30 ml of dioxane/methanol 2:1 in the presence of 1.0 g of palladium-on-charcoal (5%). When the reaction had ended, the catalyst was filtered off and the filtrate was concentrated in vacuo.

Rf value: 0.39, $CH_2Cl_2$/MeOH 5:1.

EXAMPLE 33

N-(4-Lauroylamido-4-deoxy-D-glucopyranosyl)-N-octadecyl-lauric acid amide 4.00 g of the compound described in Example 32 were dissolved in 30 ml of THF, 2.0 g of sodium carbonate were added and the compound was reacted with 1.42 g of dodecanoic acid chloride in 10 ml of THF. After 30 minutes, the mixture was diluted with methylene chloride and filtered and the filtrate was concentrated in vacuo. The syrup was purified by column chromatography (eluting agent methylene chloride/methanol=15:1).

Rf value: 0.36, $CH_2Cl_2$/MeOH 10:1.

EXAMPLE 34

N-Glucopyranosyl-N-octadecyl-palmitic acid amide

The preparation is analogous to Example 16 from N-octadecyl-glucopyranosylamine and palmitoyl chloride.

Rf value: 0.36, $CH_2Cl_2$/MeOH 9:1.

EXAMPLE 35

N-Octadecyl-N-glucopyranosyl-lauric acid amide

The preparation is analogous to Example 16 from N-octadecyl-glucopyranosylamine and lauroyl chloride.

Rf value: 0.35 $CH_2Cl_2/CH_3OH$ 9:1.

EXAMPLE 36

N-Octadecyl-N-rhammopyranosyl-stearic acid amide

The preparation is analogous to Example 22 from N-octadecyl-rhammopyranosylamine and stearoyl chloride.

Rf value: 0.39 $CH_2Cl_2/CH_3OH$ 9:1.

EXAMPLE 37

N-Octadecyl-(2-amino-2-deoxy-D-glucopyranosyl)-amine hydrochloride 6.45 g of D-glucosamine hydrochloride were dissolved in 30 ml of isopropanol and 10 ml of water at 60° C., and 12.1 g of stearylamine were added. The resulting clear solution was subsequently stirred for a further 10 minutes and then cooled to room temperature. The product which crystallized out was filtered off with suction and washed first with ethanol/water (5:2, v/v), then with ethanol and finally with ether. The residue was dried under a high vacuum.

EXAMPLE 38

N-Octadecyl-N-(2-dodecoylamido-2-deoxy-D-glucopyranosyl)-dodecanoic acid amide 4.6 g of the compound described in Example 37 were suspended in 120 ml of tetrahydrofuran, and 22.6 g of sodium carbonate were added. 4.2 g of dodecanoic acid chloride in 20 ml of tetrahydrofuran were added dropwise to the stirred suspension. The batch was evaporated in vacuo, the residue was acetylated with 50 ml of pyridine and 25 ml of acetic anhydride, the mixture was poured on to ice-water and taken up in methylene chloride and the organic phase was washed successively with dilute hydrochloric acid, saturated sodium bicarbonate solution and then with water, dried over sodium sulphate and evaporated to a syrup in vacuo. The resulting syrup was purified by column chromatography. (Eluting agent toluene/ethyl acetate=10:1, v/v). The resulting solid (melting point 86°) was dissolved in absolute methanol, 20 mg of sodium methoxide were added and the mixture was heated under reflux for 20 minutes. When the reaction had ended, the mixture was neutralized with an acidic ion exchanger and evaporated in vacuo.

Melting point: 78° C., Rf value: 0.64 in $CH_2Cl_2$/MeOH=10/1 (v/v).

EXAMPLE 39

N-Propyl-(2-amino-2-deoxy-D-glucopyranosyl)-amine hydrochloride 21.5 g of glucosamine hydrochloride were suspended in 17.7 g of n-propylamine and the suspension was warmed to 70°, until a clear solution was formed. On cooling to room temperature, the product precipitated.

EXAMPLE 40

N-Propyl-N-(2-oleoylamido-2-deoxy-D-glucopyranosyl)-oleic acid amide 5.1 g of the compound described in Example 39 were suspended in 100 ml of tetrahydrofuran, and 12.7 g of sodium carbonate were added. 12 g of oleoyl chloride in 20 ml of tetrahydrofuran were then added dropwise. When the reaction had ended, the batch was diluted with 50 ml of methylene chloride, the sodium salt was filtered off and the filtrate was washed with water, dried over sodium sulphate and evaporated in vacuo.

The resulting syrup was purified by column chromatography (eluting agent methylene chloride/methanol 5:1, v/v).

Rf value: 0.37 in CH$_2$Cl$_2$/MeOH 10:1.
$[\alpha]_D^{20}$ = 17.9° (c=1.02 in methylene chloride).

EXAMPLE 41

N-Glucopyranosyl-N-tetradecyl-stearic acid amide

The preparation is analogous to Example 12 from N-tetradecyl-glucopyranosylamine and stearoyl chloride.

Rf value: 0.25 in toluene/acetone 1:1.

EXAMPLE 42

N-Dodecyl-N-(2-amino-2-deoxy-glucopyranosyl)-amine hydrochloride 46 g of dodecylamine were melted at 60° and 31 g of glucosamine hydrochloride were added, with stirring. After cooling to room temperature, the product precipitated. The solid was extracted three times by stirring with ether and filtered off with suction and then dried under a high vacuum.

EXAMPLE 43

N-Dodecyl-N-(2-stearoylamido-2-deoxy-D-glucopyranosyl)-stearic acid amide 5 g of the compound described in Example 42 were suspended in 100 ml of tetrahydrofuran, and 8.5 g of sodium carbonate and 8 g of stearoyl chloride in 20 ml of tetrahydrofuran were added. When the reaction had ended, the product was worked up as described in Example 40. The resulting crude syrup was recrystallised from ethyl acetate.

Melting point 67°; Rf value 0.42 in CH$_2$Cl$_2$/MeOH 10/1.

EXAMPLE 44

N-Dodecyl-N-(2-lauroylamido-2-deoxy-D-glucopyranosyl)-lauric acid amide 5 g of the compound described in Example 42 were reacted with lauroyl chloride as described in Example 43.

Melting point 67°; Rf value 0.42 in CH$_2$Cl$_2$/MeOH 10/1.

EXAMPLE 45

N-Octadecyl-N-(galactopyranosyl)-amine 60 g of D-galactose were suspended in 330 ml of isopropanol and 170 ml of water and the suspension was warmed to 50°. After addition of 90 g of stearylamine, the mixture was stirred until all the amine had dissolved. On cooling, the glycosylamine crystallized out. The solid was filtered off with suction, washed successively with ethanol and ether and dried in vacuo.

EXAMPLE 46

N-Octadecyl-N-(D-galactopyranosyl)-lauric acid amide

The compound was prepared from 8.4 g of the compound described in Example 45 and 4.4 g of dodecanoic acid chloride analogously to Example 11.

Rf value: 0.22 in toluene/n-propanol 4/1 (v/v).
$[\alpha]_D^{20}$ = 11.4 (c=0.93 in methylene chloride).

EXAMPLE 47

N-Tetradecyl-N-(D-galactopyranosyl)-oleic acid amide

N-Tetradecyl-N-(D-galactopyranosyl)-amine was prepared from 30 g of D-galactose and 53 g of tetradecylamine as described in Example 45. The galactosylamine was reacted with oleoyl chloride by the method described in Example 11.

Rf value: 0.26 in toluene/n-propanol 4/1 (v/v).
$[\alpha]_D^{20}$ = 11° (c=1.0 in methylene chloride).

EXAMPLE 48

N-Octadecyl-N-mannopyranosyl-amine 20 g of D-mannose and 45 g of stearylamine were reacted to give the glycosylamine as described in Example 45.

EXAMPLE 49

N-Octadecyl-N-(D-mannopyranosyl)-lauric acid amide 8.6 g of the compound described in Example 48 were reacted with 4.4 g of dodecanoic acid chloride as described in Example 11.

Rf value: 0.25 in toluene/n-propanol 4/1 (v/v).
$[\alpha]_D^{20}$ = 11.3° (c=1.13 in methylene chloride).

EXAMPLE 50

N-Octadecyl-N-(D-mannopyranosyl)-tetradecanoic acid amide

The compound was prepared from the compound described under Example 48 and tetradecanoic acid chloride analogously to Example 11.

Rf value: 0.26 in toluene/n-propanol 4/1 (v/v).
$[\alpha]^{20}$ = 9.9° (c=1.0 in methylene chloride).

EXAMPLE 51

N-Tetradecyl-N-(D-mannopyranosyl)-oleic acid amide 20 g of D-mannose and 35 g of tetradecylamine were reacted as described in Example 45 to give N-tetradecyl-mannopyranosylamine. In a second reaction step, the glycosylamine (7.5 g) was reacted with 6.0 g of oleoyl chloride as described in Example 11 to give the glycosylamide.

Rf value: 0.29 in toluene/n-propanol 4/1 (v/v).
$[\alpha]_D^{20}$ = 10.8° (c=1 in tetrahydrofuran).

EXAMPLE 52

2-Dodecoylamido-2-deoxy-D-glucopyranose 55 g of dodecanoic acid chloride were dissolved in 170 ml of tetrahydrofuran and the solution was added dropwise to a solution of 54 g of D-glucosamine hydrochloride in 330 ml of aqueous sodium carbonate solution (20% strength), with vigorous stirring. When the addition of the acid chloride had ended, stirring was continued for a further hour, 500 ml of water were then added to the batch and the solid was filtered off with suction and washed with water. The residue was recrystallized from isopropanol/water 10/1 (v/v) and dried under a high vacuum.

EXAMPLE 53

N-Dodecyl-N-(2-dodecoylamido-2-deoxy-D-glucopyranosyl)-amine 45 g of dodecylamine and 75 ml of ethanol were added to 15 g of the compound described in Example 52 and the mixture was warmed at 70°, with stirring. After

15 a clear solution had formed, the mixture was cooled to room temperature and crystallized overnight. The solid which had precipitated was filtered off with suction, washed once with ethanol and three times with ether and dried in vacuo.

EXAMPLE 54

N-Dodecyl-N-(2-dodecoylamido-2-deoxy-D-glucopyranosyl)-stearic acid amide 4 g of the compound described in Example 53 were dissolved in 100 ml of tetrahydrofuran, and 4.8 g of sodium carbonate were added. 3.45 g of stearyl chloride, dissolved in 20 ml of tetrahydrofuran, were added dropwise to this suspension, with stirring. Stirring was continued for 30 minutes, the mixture was diluted with 50 ml of methylene chloride and the solid was filtered off with suction. The residue was washed with methylene chloride. The organic solvent phases were combined and concentrated in vacuo. The resulting syrup was purified by chromatography. (Eluting agent: methylene chloride/methanol 20/1 (v/v)).

Rf value: 0.55 in methylene chloride/methanol 10/1 (v/v).

$[\alpha]_D^{20} = 15.8°$ (c=1.05 in methylene chloride).

EXAMPLE 55

N-Dodecyl-N-(2-acetamido-2-deoxy-D-glucopyranosoyl)-tetradecanoic acid amide 26 g of N-acetylglucosamine were dissolved in 100 ml of ethanol and 60 ml of water and the solution was warmed to 60°. 37 g of dodecylamine were added and the mixture was stirred until a clear solution had formed. After cooling to room temperature, the glycosylamine crystallized out. The crystal sludge was filtered off with suction, washed with ethanol and then with ether and dried in vacuo. 3 g of the solid were suspended in 50 ml of tetrahydrofuran, 3.3 g of sodium carbonate were added, and 1.9 g of tetradecanoic acid chloride in 10 ml of tetrahydrofuran were added. When the reaction had ended, the mixture was diluted with 30 ml of methylene chloride and filtered and the filtrate was evaporated in vacuo. The resulting syrup was purified by chromatography (eluting agent methylene chloride/methanol 20/1, (v/v)).

Rf value: 0.21 in methylene chloride/methanol 10/1 (v/v).

EXAMPLE 56

N-Dodecyl-N-(2-acetamido-2-deoxy-D-glucopyranosyl)-stearic acid amide 3 g of N-(2-acetamido-2-deoxy-D-glucopyranosyl)-dodecylamine, the preparation of which is described in Example 55, were reacted with stearoyl chloride as described in Example 55.

Rf value: 0.23 in methylene chloride/methanol (10/1 (v/v).

EXAMPLE 57

N-Octadecyl-N-(2-acetamido-2-deoxy-D-glucopyranosyl)-tetradecanoic acid amide

The preparation is analogous to Example 20 from N-acetylglucosamine, stearylamine and tetradecanoic acid chloride.

Rf value: 0.25 in toluene/isopropanol 4/1 (v/v).

$[\alpha]_D^{20} = 16.9°$ (c=1 in tetrahydrofuran).

EXAMPLE 58

N-Dodecyl-N-(D-mannopyranosyl)-stearic acid amide

The compound was prepared from D-mannose, dodecylamine and stearoyl chloride analogously to Example 11.

Rf value: 0.28 in toluene/n-propanol 4/1 (v/v).

$[\alpha]_D^{20} = 11.4°$ (c=1 in tetrahydrofuran).

EXAMPLE 59

N-Dodecyl-N-(D-galactopyranosyl)-stearic acid amide

The compound was prepared from D-galactose, dodecylamine and stearoyl chloride analogously to Example 11.

Rf value: 0.28 in toluene/n-propanol 4/1 (v/v).

$[\alpha]_D^{20} = 4.4°$ (c=1 in methylene chloride).

EXAMPLE 60

N-Tetradecyl-N-(2-amino-2-deoxy-D-glucopyranosyl)-stearic acid amide hydroacetate 3.1 g of 2-(benzyloxycarbonylamino)-2-deoxy-D-glucose were dissolved in 40 ml of dimethylformamide, 3.2 g of tetradecylamine were added and the mixture was warmed at 80° C. for 4 hours, under a water pump vacuum. The mixture was cooled to room temperature, diluted with 50 ml of tetrahydrofuran and stirred in the presence of 5 ml of ion exchanger SC 108 (H+ form). The exchanger resin was filtered off and 1 g of sodium carbonate and 3.3 g of stearoyl chloride were added to the filtrate. After the mixture had been stirred for five hours, the solid constituents were filtered off and the filtrate was evaporated in vacuo. The resulting syrup was purified by column chromatography on silica gel (eluting agent methylene chloride/methanol=20:1).

The main product from the separation was dissolved in 20 ml of dioxane, 20 ml of methanol and 20 ml of glacial acetic acid and hydrogenated in the presence of 1 g of palladium-on-charcoal (5%). When the uptake of hydrogen had ended, the catalyst was filtered off, the filtrate was evaporated to a syrup and the syrup was evaporated with ethanol several times for complete removal of the acetic acid.

$[\alpha]_D^{20} = +10.2°$ (c=0.95 in tetrahydrofuran).

It will be understood that the specification and examples are illustrative but not limitative of the present invention and that other embodiments within the spirit and scope of the invention will suggest themselves to those skilled in the art.

We claim:

1. A method of combating rheumatic diseases which comprises adminstering to a patient afflicted therewith an amount effective to combat such disease of a compound of the formula

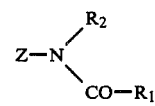

in which
Z is a glycosyl radical bonded via the anomeric carbon atom,
R₁ is hydrogen; an alkyl or alkenyl radical with 1 to 21 carbon atoms; an alkyl or alkenyl radical with 1 to 21 carbon atoms interrupted b y 0, S or N; an alkyl or alkenyl radical with 1 to 21 carbon atoms and substituted by halogen, hydroxy, oxo, amino, phenyl nitrophenyl, lower alkyl phenyl or halophenyl; or an alkyl or alkenyl radical with 1 to 21 carbon atoms interrupted by 0, S or N and substituted by halogen, hydroxy, oxo, amino, phenyl nitrophenyl, lower alkyl phenyl or halophenyl; and $R_2$ is hydrogen; a saturated aliphatic, cycloaliphatic, alkylcycloaliphatic or araliphatic radical with up to 30 carbon atoms; a saturated aliphatic, cycloaliphatic, alkylcycloaliphatic or araliphatic radical with up to 30 carbon atoms, interrupted by O, S, N, NH or N-lower alkyl; a saturated aliphatic, cycloaliphatic, alkylcycloaliphatic or araliphatic radical with up to 30 carbon atoms interrupted by O, S, N, NH or N-lower alkyl; a saturated aliphatic, cycloaliphatic, alkylcycloaliphatic or araliphatic radical with up to 30 carbon atoms substituted by up to 5 oxygen-containing groups or halogen atoms; or a saturated aliphatic, cycloaliphatic, alkylcycloaliphatic or araliphatic radical with up to 30 carbon atoms interrupted by O, S, N, NH or N-lower alkyl and substituted by up to 5 oxygen-containing groups or halogen atoms.

2. The method according to claim 1, in which $R_1$ is an alkyl or alkenyl radical with up to 20 carbon atoms.

3. The method according to claim 1, in which $R_2$ is an alkyl or alkenyl radical with up to 20 carbon atoms.

4. The method according to claim 1, in which Z is a monosaccharide radical, or is a monosaccharide radical which is substituted by an acylamide group, in which acyl is derived from a carboxylic acid with 1 to 20 C atoms.

5. The method according to claim 1, wherein the compound is N-glucosyl-N-octadecyl-dodecanoic acid amide.

6. The method according to claim 1, wherein the compound is N-dodecyl-N-(2-acetamido-2-deoxy-D-glucopyranosyl)-stearic acid amide.

7. The method according to claim 1, wherein the compound is N-tetradecyl-N-(2-amino-2-deoxy-D-glucopyranosyl)-stearic acid amide.

8. The method according to claim 1, in which $R_1$ is methyl, ethyl, propyl, i-propyl, butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, ethylpentyl, methyldecyl, i-propyldecyl, methyltridecosyl, vinyl-prop-1-enyl, prop-2-enyl, i-butenyl, but-1-enyl, but-2-enyl, pent-1-enyl, pent-2-enyl, pent-3-enyl, pen-4-enyl, hex-1-enyl, hex-2-enyl, hex-3-enyl, hex-4-enyl, hex-5-enyl, dec-1-enyl, dec-5-enyl, dec-9-enyl, heptadec-8-enyl, buta-1,3-dienyl, penta-1,3-dienyl, penta-1,4-dienyl, penta-2,4-dienyl, heptadecane-8,11-dienyl, heptadecane-8,11,14-trienyl, methoxy-ethyl, 2-(2-methoxyethoxy)-ethyl, 2-[2-(2-methoxyethoxy)-ethoxy]-ethyl, hydroxyheptadecenyl, oxobutyl, aminodecyl, N-methylaminodecyl, fluoromethyl, β-hydroxytridecyl, mercaptoethyl, and $R_2$ is methyl, propyl, hexyl, decyl, undecyl, dodecyl, tridecyl, tetradecyl, pentadecyl, headecyl, heptadecyl, octadecyl, nonadecyl, docosyl, myricyl, ethylhexyl, isobutyl, propenyl, octenyl, hexadienyl, docosenyl, dimethylhexenyl, 2-(cyclohexyl)-ethyl, hydroxypropyl, hydroxydimethyloctyl, methoxybutyl, butoxypropyl, ethoxyethoxy-ethyl, 2-(N-morpholino)-ethyl, trifluoromethylethyl, benzyl, phenethyl, phenylhexyl or benzyl, phenethyl or phenylhexyl substituted on the benzene ring by trifluoromethyl, halogen, hydroxyl, $C_{1-3}$-alkyl or $C_{1-3}$-alkoxy.

* * * * *